United States Patent [19]

Rivola et al.

[11] Patent Number: 5,404,104
[45] Date of Patent: Apr. 4, 1995

[54] DEVICE AND METHOD FOR MONITORING AND LOCATING DEFECTS IN, AND DETACHMENT OF, THE PROTECTIVE COVERING OF UNDERGROUND OR IMMERSED METAL STRUCTURES OR PIPELINES

[75] Inventors: Luigi Rivola, San Donato Milanese; Sebastiano Di Liberto, San Giuliano Milanese; Giacomo Capitelli, Milan; Lucio Di Biase, San Donato Milanese, all of Italy

[73] Assignees: Agip S.p.A. - Snam S.p.A.; Eniricerche S.p.A., both of Milan, Italy

[21] Appl. No.: 28,212

[22] Filed: Mar. 9, 1993

[30] Foreign Application Priority Data

Mar. 11, 1992 [IT] Italy ............................... MI92A0557

[51] Int. Cl.⁶ ............................................. G01N 27/00
[52] U.S. Cl. .................................. 324/425; 324/71.1; 204/153.11
[58] Field of Search .............. 324/525, 71.1, 71.2, 324/713, 715, 425; 204/404, 153.11; 307/95

[56] References Cited

U.S. PATENT DOCUMENTS

| | | | |
|---|---|---|---|
| 3,649,492 | 3/1972 | Marsh et al. | 324/71.2 |
| 4,003,815 | 1/1977 | Ikeda et al. | 324/71.2 |
| 4,080,565 | 3/1978 | Polack | 324/71.1 |
| 4,151,458 | 4/1979 | Seager . | |
| 4,481,474 | 11/1984 | Gerrit | 324/71.2 |
| 4,591,792 | 5/1986 | Birchmeier et al. | 324/425 |
| 4,611,175 | 9/1986 | Kumar et al. . | |
| 5,126,654 | 6/1992 | Murphy et al. | 324/71.2 |
| 5,144,247 | 9/1992 | Speck | 324/425 |
| 5,216,370 | 6/1993 | Bushman et al. | 324/425 |

FOREIGN PATENT DOCUMENTS

| | | | |
|---|---|---|---|
| 0022890 | 2/1979 | Japan | 324/71.2 |
| 0197858 | 8/1991 | Japan | 324/71.2 |
| 2224575 | 9/1990 | United Kingdom . | |

OTHER PUBLICATIONS

Patent Abstract of Japan Oka Motoki, et al. vol. 10, No. 215 (P-481) Jul. 26, 1986, JP-A-61 053 560 (Nippon Steel Corp) Mar. 17, 1986.

Primary Examiner—Maura K. Regan
Attorney, Agent, or Firm—Oblon, Spivak, McClelland, Maier & Neustadt

[57] ABSTRACT

A method for monitoring the state of, and for locating any detachment of, the protective covering of immersed or buried pipelines or other metal structures subjected to cathodic protection with constant current, on the basis of the overall electrical resistance offered by the pipeline/covering/ground system, consisting of applying local sinusoidal wave excitation currents of different frequencies to the pipeline and measuring the corresponding voltage responses, then comparing the measured responses of the system to determine, on the basis of response differences or coincidences at the various frequencies, whether within the portion under consideration there is detachment with corrosion underway or whether there is simple covering decay.

10 Claims, 8 Drawing Sheets

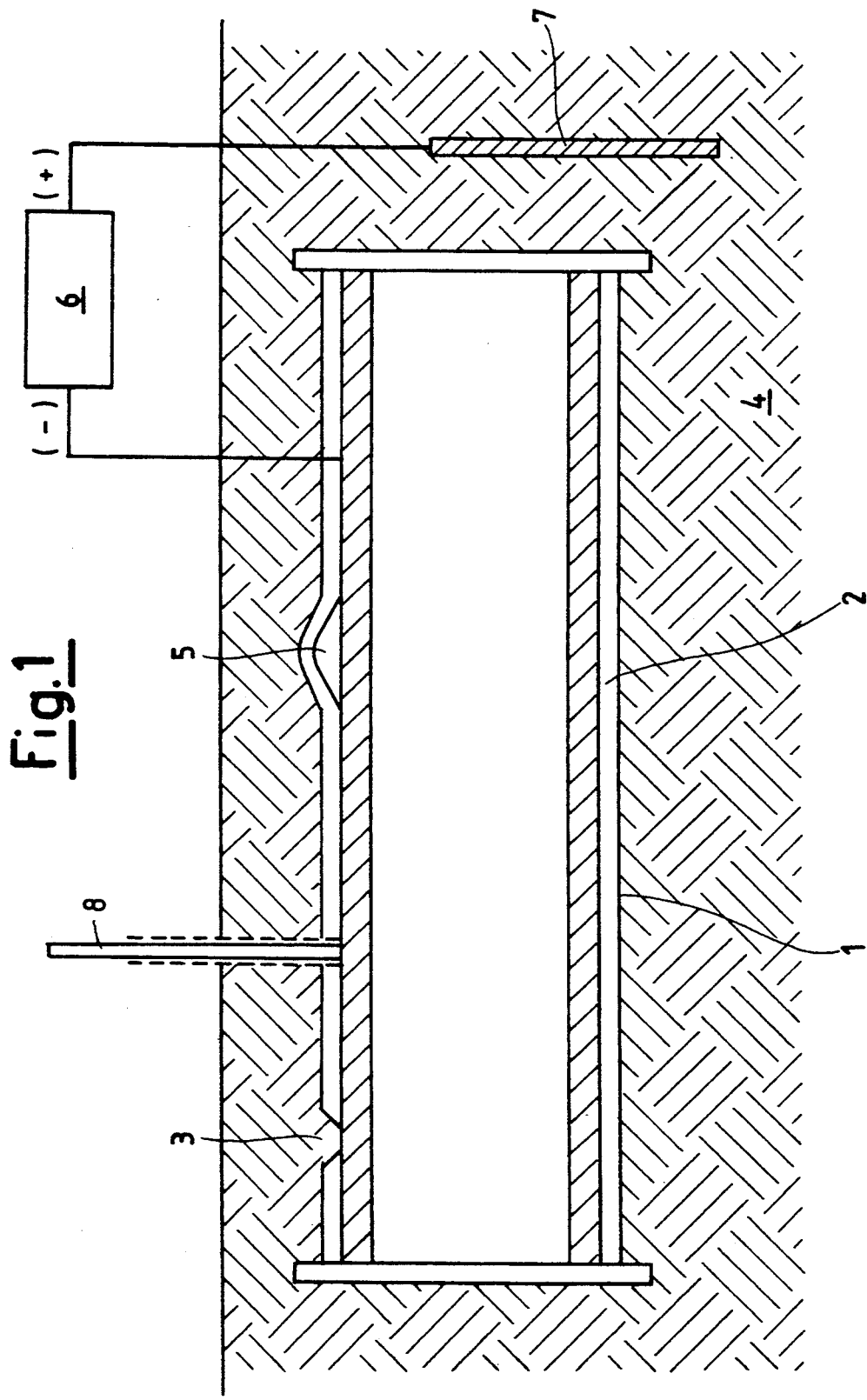

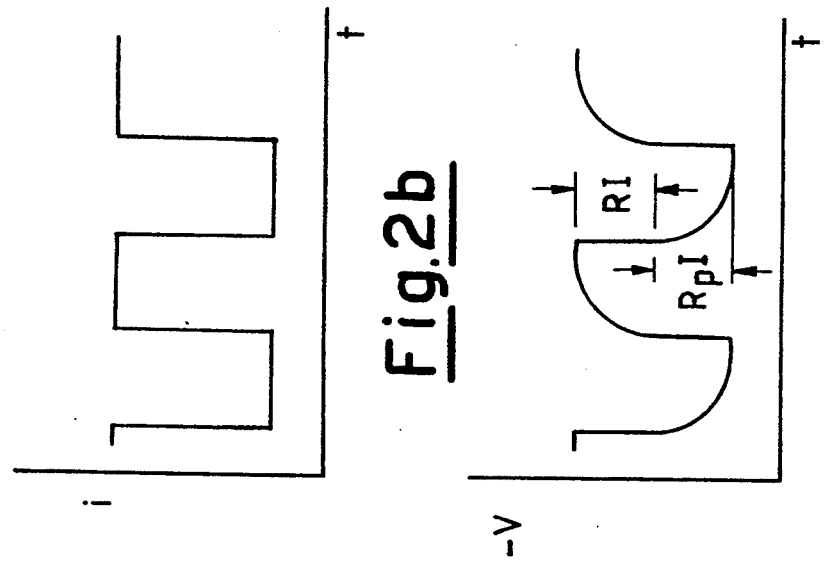
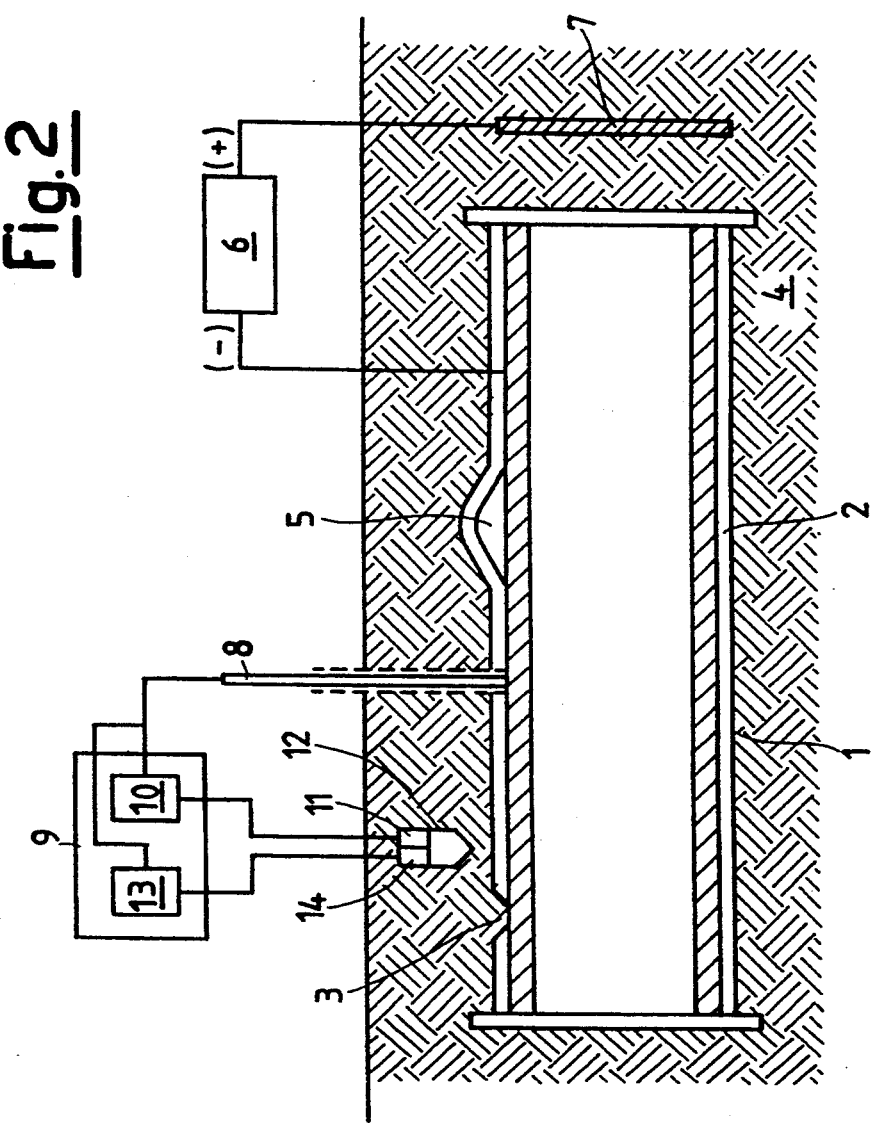

Fig.5a  Fig.5b  Fig.5c
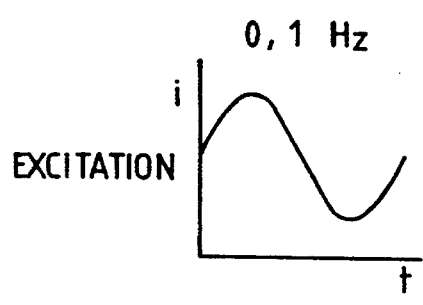
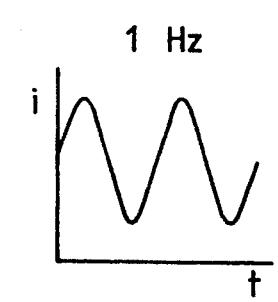
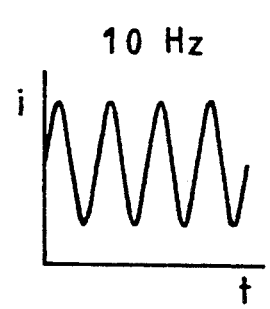
Fig.5d  Fig.5e  Fig.5f
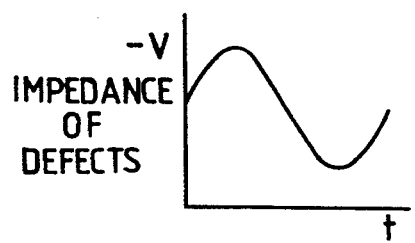
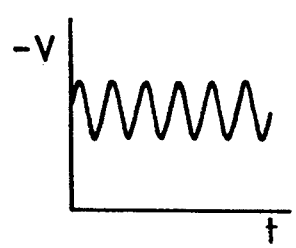
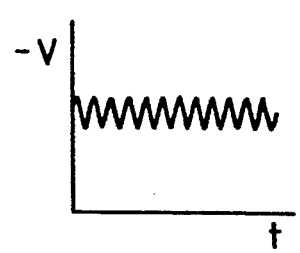

EXCITATION

PRESENCE OF DEFECTS

PRESENCE OF DETACHMENTS

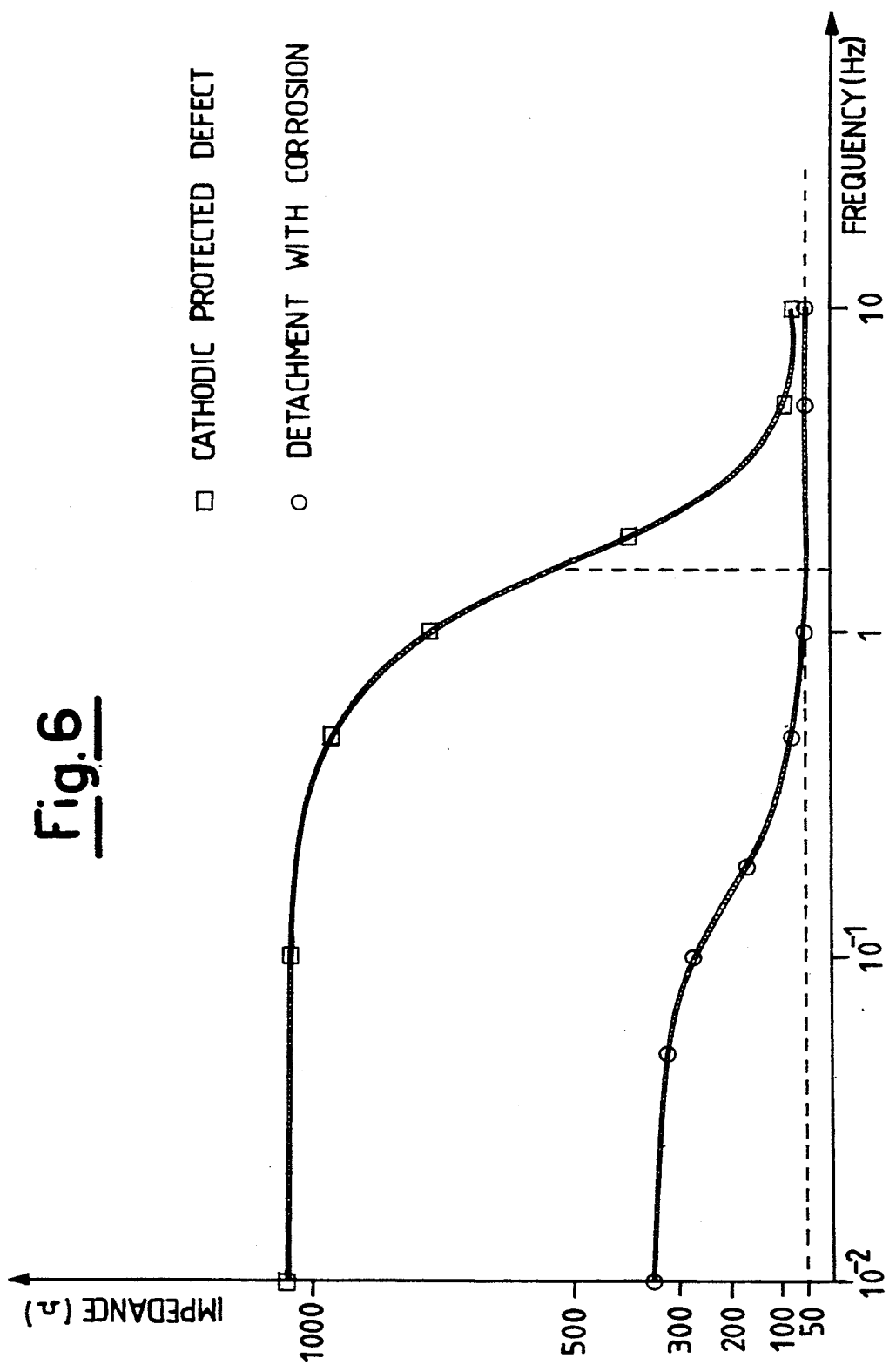

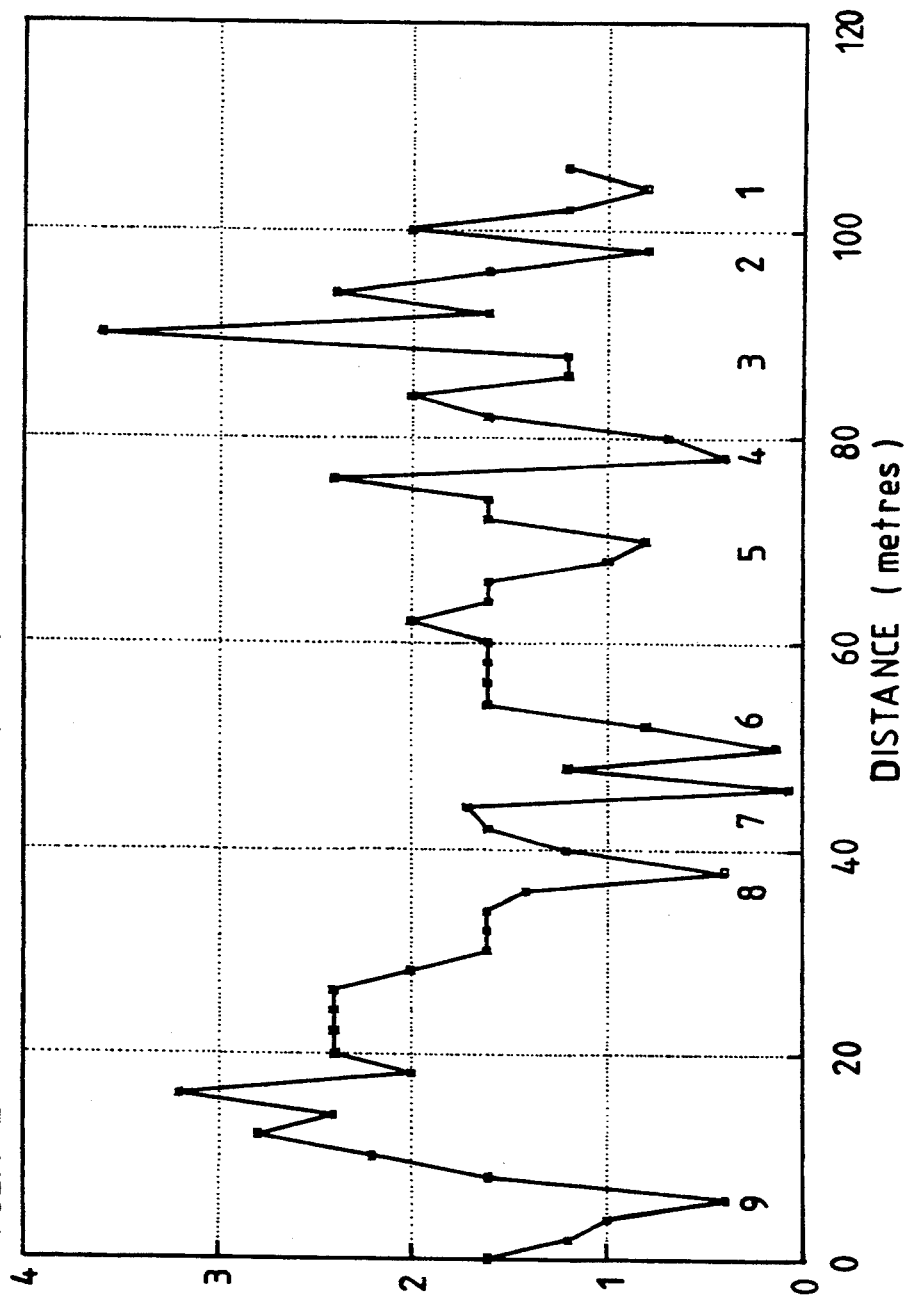

DEVICE AND METHOD FOR MONITORING AND LOCATING DEFECTS IN, AND DETACHMENT OF, THE PROTECTIVE COVERING OF UNDERGROUND OR IMMERSED METAL STRUCTURES OR PIPELINES

BACKGROUND OF THE INVENTION

1. Field of the Invention

This invention relates to the protection of underground or immersed structures exposed to wet corrosion. In industrial practice many metal structures suffer from this technical problem, for example underground fuel storage tanks, off-shore structures, fluid transporting pipelines such as water, gas and oil pipelines, and other infrastructures for industrial, civil or military use.

The present invention is described with reference to underground pipelines, and involves one of its most difficult and interesting applications, but without in any way limiting it to this specific application.

2. Discussion of the Background

Liquid or gas transporting pipelines, such as gas, water or oil pipelines, are formed by welding together lengths of metal pipe, generally of steel, the continuous pipeline assembled in this manner being laid in its final seat, generally consisting of a sufficiently deep trench, and then covered in order to recreate the pre-existing environment and hence not hinder its further use. The assembled continuous pipeline is provided with protection against wet corrosion, as the environment in which the underground or immersed pipeline lies is very aggressive towards ferrous materials.

The integrity and preservation of the pipeline during its entire operating life must be ensured, both because of its high construction cost and, in particular, because fluid leakages must be prevented as they can cause danger, pollution or serious disturbance, in addition to representing an economical burden. The protection generally used consists of two different types of protection in mutual cooperation, namely "passive" protection consisting of a covering which isolates the pipeline from the surrounding environment, and "cathodic" protection which applies an electric potential for inhibiting possible electrochemical reactions which could attack the pipeline metal to the extent of forming a through hole.

The "passive" protection is generally formed by applying a continuous covering to the properly cleaned pipeline. This covering can be of two main types, the first type being coverings of hydrocarbon materials such as asphalts and bitumens which are generally applied hot in a number of layers together with fibrous material reinforcements, and the second type being synthetic polymer coverings such as polyethylene, polyvinylchloride and epoxy polymers, these being applied in the form of strips wound spirally about the pipeline and superimposing the side edges, or by die-casting. Web, felt or card made of glass wool, asbestos or other non-rotting fibrous material are used as protection and reinforcement. This protection is not on its own sufficient to protect an underground or water-immersed pipeline for the required time.

In this respect, the following should be noted:

no material is free of a certain porosity and permeability, even if perfectly applied, and hence a certain diffusion of the chemical species responsible for corrosive attack takes place through the protective layer, even if very slight;

the sequence of operations involved in the preparation, covering, lifting, laying and burying of the pipeline can result in immediate slight damage or imperfections to the applied covering, these defects then triggering corrosion phenomena;

the hydrocarbon or polymer materials and their reinforcements have a chemical and physical stability which is very high but is not absolute, particularly in relation to temperature or humidity changes;

natural phenomena, such as earthquakes, landslips and floods, and accidental events can damage the pipeline passive protection. The "cathodic" protection protects the pipeline at those points in which porosity, damage or imperfect application of the covering have left the metal surface exposed to corrosive attack.

The variation in the state of the passive protection covering on the pipeline can be monitored by the method described in EP Patent Application Public. No. 0 411 689 in the name of the present applicant. Detection of local damage due to accidental events can be effected by the method described in EP application Public. No. 0 495 259.

According to these methods, the cathodic protection current applied to the pipeline is modulated by square waves. The application of square wave signals enables the resistive components and the capacitive components constituting the overall impedance of the pipeline-ground system to be separated and determined.

The present invention relates to the monitoring and location of any detachment of the protective covering from the metal walls of buried or immersed pipelines, due to various causes such as imperfect application of the covering, movement and deformation of the pipeline, ageing and brittling of the covering materials or applied adhesives exposed to an aggressive environment, or the development or seepage of gas or vapour between the pipeline and sheath. Such detachment is generally concentrated, and in contrast to normal covering decay it requires urgent local repair, otherwise it could cause rapid local corrosion to the extent of putting the entire pipeline out of use.

To highlight the characteristics of this problem, FIG. 1 shows a pipeline portion 1 with, towards the left, a defect in the covering 2 exposing a zone 3 of the metal wall, which is thus in contact with the ground 4. Towards the right there is a detachment of the covering 2 which creates a bubble between the wall and the covering, leaving a wall zone 5 exposed to corrosion. The pipeline is provided with a cathodic protection current generator 6 connected to the ground 4 via the earth plate 7. Numerous appendices 8 are distributed along the pipeline for the electrical connection.

At the defect in the zone 3 the cathodic protection current replaces the protection offered by the covering as there is electrical continuity between the ground 4 and the pipeline, the pipeline 1 therefore being still protected and not subject to corrosion.

In contrast, due to the effect of microporosity or of small gaps, over the long term there is migration into the bubble in the zone 5 of moisture, aggressive substances and aggressive microorganisms (sulphate-reducer bacteria colonies are particularly dangerous) which trigger concentrated corrosion on the metal wall of the zone 5.

Such corrosion can result in the development of gas phases which further extend the bubble and the corrosive attack zone. In contrast to the preceding case the metal wall does not have effective electrical continuity with the ground 4 because of the screening provided by the interposed raised covering 2, with the result that the cathodic protection current cannot effectively replace the covering in protecting the pipeline. It is therefore necessary to determine and locate early on those zones in which the covering has become detached from the pipeline in order to remedy this before such corrosion irreparably damages the metal walls of the pipeline.

SUMMARY OF THE INVENTION

In this respect, tile main problem which the present invention solves is that of monitoring and locating any detachment of protective covering from a pipeline or a metal structure, or more precisely any corrosion underway in those zones in which such detachment has taken place. According to the invention, the protective covering of immersed or buried pipelines or other metal structures subjected to cathodic protection with constant current is monitored for detecting and locating the position of detachments or defects therein on the basis of the overall electrical resistance offered by the pipeline/covering/ground system. The invention involves applying local sinusoidal wave excitation currents of different frequencies to the pipeline and measuring the corresponding voltage responses, then comparing the measured responses of the system to determine, on the basis of response differences or coincidences at the various frequencies, whether within the portion under consideration there is detachment with corrosion underway or whether there is simply covering decay.

BRIEF DESCRIPTION OF THE DRAWINGS

FIG. 1 illustrates a portion of a pipeline having a defect and a detachment in a covering thereof and a conventional apparatus for detecting their locations;

FIG. 2 shows a portion of a pipeline having a defect and detachment in the covering therefore and an apparatus for detecting their locations according to an embodiment of the present invention;

FIG. 6 shows a graph of variations in the impedance between the pipeline and ground as a function of the frequency of the sinusoidal excitation current wave; and FIG. 7 shows a graph plotting polarization resistance vs. distance across the length of a pipeline in accordance with the present invention.

DETAILED DESCRIPTION OF THE PREFERRED EMBODIMENTS

Figure 3A:
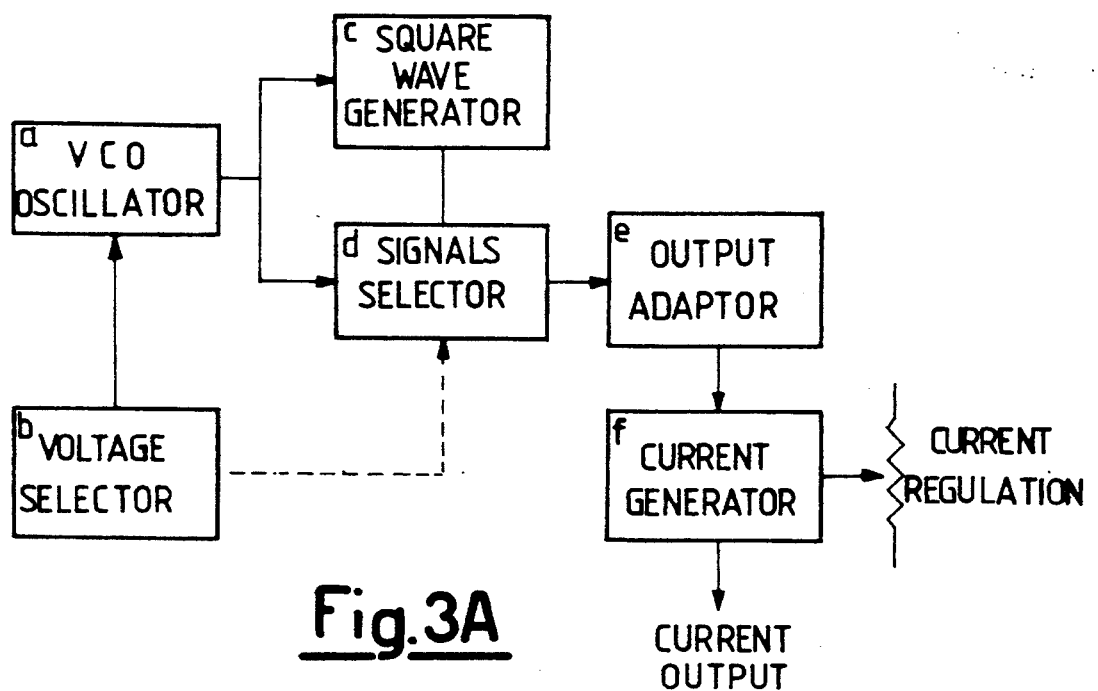
FIG. 3A and 3B show different embodiments of the generator circuit according to the invention which is included in the measurement system in FIG. 2.

The device and method of the present invention are described by way of non-limiting example with reference to a typical embodiment shown as a block diagram in FIG. 2.

The device of the invention consists of a measurement system 9 to be applied to the pipeline portion which, as illustrated in FIG. 1, is protected cathodically by a fixed current generator 6 connected to the ground via the earth plate 7.

The measurement system 9 consists of a generator circuit 10 generating an oscillatory electrical excitation current signal and connected both to the pipeline 1 via one of its appendices 8 and to the earth plate 11 of a two-pole stake 12, and a circuit 13 for measuring the signals representing the potentials induced by the excitation currents and connected both to the reference electrode 14 representing the other pole of the two-pole stake 12 and to the pipeline preferably by the actual cable which connects the generator circuit 10 to the appendix 8.

The stake 12 is buried in the ground surrounding that portion of the pipeline to be monitored.

The upper half of the right hand side of FIG. 2 shows by way of example the excitation diagram when using a square wave current, and the lower half shows the corresponding diagram for the potential induced in that portion of the pipeline subjected to excitation.

Figure 3B:
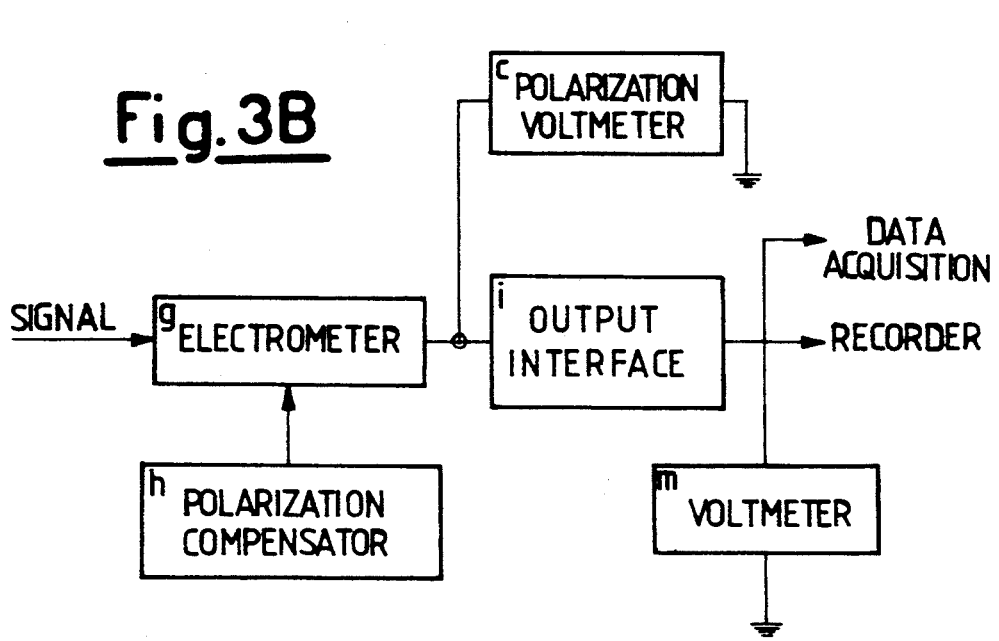
Figure 4A:
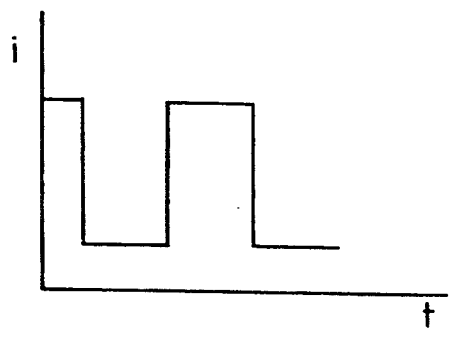
FIG. 4 shows various potential waveforms detected upon electrically monitoring a pipeline using the apparatus according to the invention.
Figure 4B:
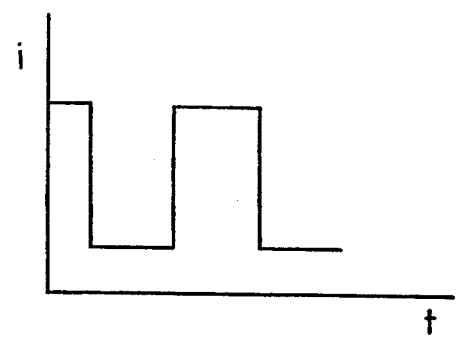
Figure 4C:
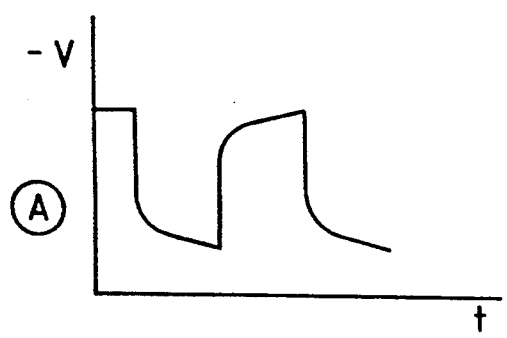
Figure 4D:
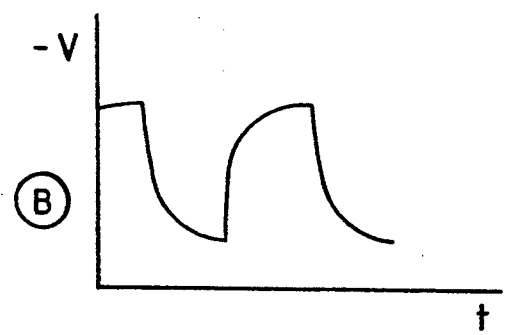
Figure 4E:
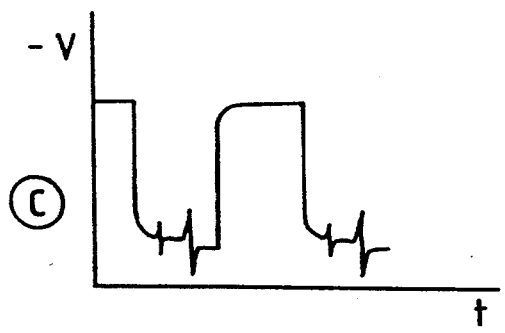
Figure 4F:
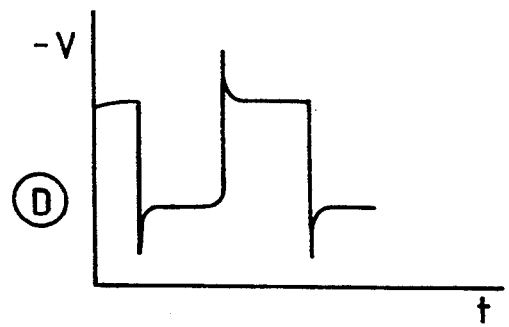
Figure 5G:
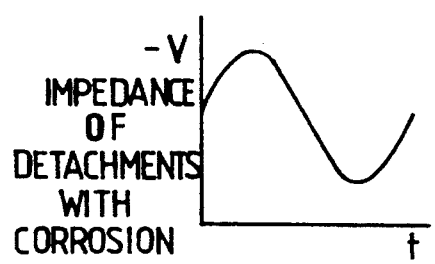
FIG. 5 shows different sinusoidal frequency responses corresponding to a plurality of types of defects or detachments of a pipeline covering.
Figure 5H:
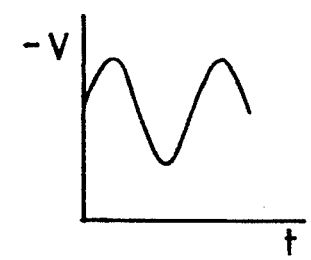
Figure 5I:
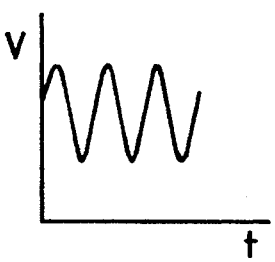
Figure 5L:
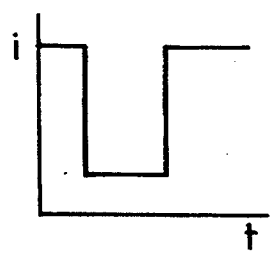
Figure 5M:
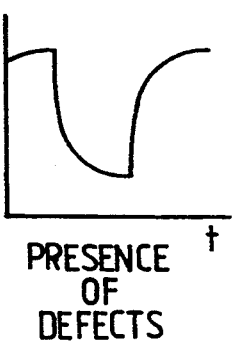
Figure 5N:
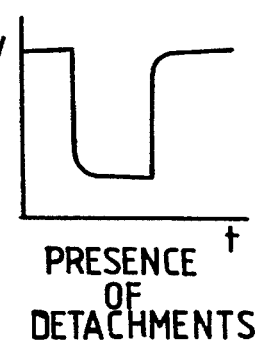

FIG. 3A and 3B shows by way of non-limiting example typical embodiments of the generator circuit 10 for generating the electrical current signal transmitted to the earth plate 11 of the two-pole stake 12 (FIG. 3A) and the circuit 13 for measuring the signal deriving from the potential induced in the pole 14 of the stake 12, constituting the reference electrode (FIG. 3B).

In the block diagram of FIG. 3A the current signal generation circuit is formed from the following components:
a) Voltage controller oscillator (VCO) for generating sinusoidal waves,
b) Direct current voltage selector for frequency control,
c) Square wave generator with equal half-periods,
d) Selector for switching the signals to be fed to the output adaptor,
e) Output adaptor for signal mixing,
f) Current generator for feeding excitation signals to the pipeline.

This circuit can be built from commercially available electronic components and enables both square wave and sinusoidal wave oscillatory excitation current signals of predetermined frequency and intensity to be fed.

In the block diagram of FIG. 3B, the circuit for measuring the correspondingly generated potential signal is formed from the following components:
g) Impedance transducer electrometer for measuring the potential between the reference electrode and the pipeline,
h) Compensator for the pipeline cathodic polarization,
i) Interface for adapting the signals to the various users (recorder, voltmeter and data acquisition),
l) Voltmeter for measuring the pipeline cathodic polarization potential,
m) Output signal voltmeter.

This circuit can be built from commercially available electronic components and enables the voltage signals generated by the excitation with the current signals to be measured. In industrial applications and field experiments conducted using the methods of the preceding European Patent Appln. Public. No.0 411 889 and No.0 495 259 it was found that in actual field applications the square-wave modulated current generates a corresponding potential shown in FIG. 4.

The shape of the voltage square wave shows a vertical rectilinear portion reflecting the ohmic loss (R.I.) and an oblique descending portion as far as ,equilibrium, the amplitude of which reflects the value $R_p.I$ (where $R_p$ indicates polarization resistance) which is useful for detecting corrosion phenomena.

Measuring the ohmic loss over a discrete portion of the pipeline enables the average state of its protective covering to be determined, i.e. relative extension of distributed defects and overall ageing of the covering in accordance with EP application Public. No. 0 411 889, or identification of an accidental event which has given rise to one or more concentrated defects in accordance with EP appln. Public No. 0 495 259. The defects discovered in this manner consist, as stated, of gaps in the protective covering which put the pipeline into contact with the ground. The depth of the minimum R.I. values is hence related to the extension of the defects.

FIG. 4 shows different possible configurations, in field applications, to the voltage response to disturbances of various origins, the ohmic loss and the polarization resistance not always being precisely separable and measurable. Diagram A of FIG. 4 shows the typical variation in the potential response signal corresponding to square wave current excitation, in which the ohmic component R.I. and the reactive component $R_pI$ are separable. The subsequent diagrams show some examples of actual behavior. Diagram B shows a case in which the two components are not clearly separable, the ohmic component being relatively small, diagram C shows the effect of disturbance by external electrical fields which do not allow the response signal to reach stability, and diagram D shows the effect of equalization currents.

Information relative to the electrochemical parameters involved in detachment and corrosion phenomena is contained in the pattern of the oblique part of the square wave form which represents the time $R_p$. $C_{d1}$ for the discharge of the energy accumulated in the double layer, where $C_{d1}$ indicates the capacitance of the double layer. From experimental tests it has been found that the rate at which equilibrium of the minimum voltage value is reached is much greater in the case of covering defects still protected by the cathodic protection current (equilibrium is generally reached after a time of about one second) compared with the case in which covering detachment arises no longer protected by the cathodic protection current (equilibrium is reached after five-ten seconds).

An examination of the oblique part of the square wave form is often useless because of the presence of disturbances such as dispersed currents, equalization currents or other uncontrollable phenomena.

It has now been found that if sinusoidal excitation currents of different frequencies are applied to the pipeline, voltage responses are obtained which enable both the pipeline defects and detachments to be determined.

The selectivity in sensing defect/detachment phenomena is determined by their different amplitude responses to the different sinusoidal wave frequencies, as shown in FIG. 5. This corresponds to the fact that in the case of a defect (local gap in the covering) the low $C_{d1}$ values and the high $R_p$ values determine a considerable variation in the amplitudes of the sinusoidal voltage response waves as the frequency varies for example between 10 Hz and 1 Hz. In contrast, in the case of a detachment (bubble between covering and wall without appreciable gaps) with corrosion underway the high $C_{d1}$ values and the low $R_p$ values determine a substantial constancy in the amplitudes of the sinusoidal voltage response waves as the frequency varies for example between 10 Hz and 1 Hz.

In other words, the application of sinusoidal currents of different frequencies gives rise to a spread of voltage responses in the case of defects and to substantially coincident responses in the case of detachment.

A square wave excitation part inserted into the train of modulation waves of the current applied to the pipeline portion represents a means for controlling the applied frequency field and enables the ohmic losses R.I. of the pipeline to be determined. Both for defects and detachments, the ohmic loss itself, determined on the basis of the vertical part of the wave form of the potential induced by the applied square wave, must assume an amplitude equal to that produced by the sinusoidal current wave applied at the highest frequency, whereas the total amplitude of the wave form of the potential induced by the applied square current wave must assume a value equal to that produced by the sinusoidal current wave applied at the lowest frequency, If this does not happen, the scanned frequency range must be expanded until this coincidence is obtained, From experiments conducted up to the present time, a frequency range from 10 to $10^{-2}$ Hz has been found sufficient to obtain suitable results, applying very low currents (a few mA) to obtain voltage responses sufficient for measurement.

A comparison of the potential responses for the various applied sinusoidal current frequencies shows whether a defect (spread values) or a detachment (concentrated values) is concerned. FIG. 5 shows by way of example the variations in the various voltage responses to excitation both by square wave currents and by sinusoidal currents at those different frequencies, as heretofore described, suitable for determining and locating imperfections in the protection of pipelines, in accordance with the present invention, FIG. 6 shows the variation in the impedance between the pipeline and ground as a function of the frequency of the sinusoidal excitation current wave, The upper curve shows the variation in the defect impedance, which varies considerably as the frequency varies, whereas the lower curve shows the variation in impedance deriving from detachment with corrosion, this varying much less as the frequency varies.

The excitation currents to be applied to the pipeline in the method of the present invention consist of at least two trains of sinusoidal current waves of between 0.1 and 10 mA at frequencies of between $10^{-3}$ and 30 Hz, the frequency ratio being between 10 and 1000 and preferably between 40 and 100. The useful duration of each wave train is from 3 to 10 cycles. These currents are superimposed on the normal cathodic protection current and can be accompanied by square wave excitation trains for verifying that the frequencies used are correct for the case under examination, in accordance with the aforegoing criteria. The method according to the invention for monitoring and locating detachments in the covering of a pipeline comprises the following stages.

Before taking measurements, if appropriate the cathodic protection current modulation is interrupted in accordance with said preceding patent applications of the present applicant, while maintaining cathodic protection at a non-modulated fixed current intensity.

The measurement system 9 is connected to one of the appendices 8 of the pipeline portion to be monitored and the two-pole stake 12 is buried in the ground above the pipeline, which is connected to the system 9.

The generator 10 feeds excitation currents in the already described manner, for example two trains of successive sinusoidal waves at 0.1 and 10 Hz for 5 cycles, the meter 13 recording the corresponding voltage responses.

According to a preferred embodiment of the invention, the suitability of the chosen excitation frequencies is checked by also applying, possibly irregularly at a few points along the pipeline, square wave excitation current trains of equal intensity to verify that the, R.I. signal responses to the square wave coincide substantially with the amplitude of the signal obtained with the highest frequency sinusoidal current, and that the total response amplitudes to the square wave coincide substantially with the amplitude of the signal obtained with the lowest frequency sinusoidal current. The frequency of these square wave trains is 0.1–0.01 Hz.

The measurement is repeated after extracting the stake and moving it a short length along the pipeline, for example in steps of a few meters, preferably 2–10 meter steps, and then reburying it in the overlying ground, then emitting the same excitation current signals and measuring the voltage responses. To monitor the entire pipeline in discrete steps, the length of the cable which connects the system 9 to the appendix 8 must be equal to at least one half of the distance separating two consecutive appendices 8. After taking measurements along the portion allowed by the connection, the device 9 is moved and reconnected to the pipeline to monitor its next portion.

When all the measurements have been taken the data are compared. The peak-to-peak voltage differences between the signals measured at low frequency (0.1–0.01 Hz) and those measured at high frequency (5–100 Hz) are divided by the intensity of the fed currents (0.1–10 mA) and the results are referred to the measurement point, for example on a diagram. The values obtained indicate the polarization resistance $R_p$ corresponding to the point at which the stake was positioned. Minimum, values correspond to points at which corrosion is underway, and the depths of these minima are related to the intensity of the corrosion.

EXAMPLE

The device and method of the invention were tested in the field for monitoring a portion of a 42" methane pipeline in which possible corrosion damage had already been indicated by the passage of an "intelligent pig" which had run through its interior.

The tests were conducted with a two-pole stake consisting of a finned micro-earthing plate of AISI 304 steel and a Ta-$Ta_2O_5$ reference electrode. The length of the stake was about 70 cm. The generator circuit 10, formed in accordance with the scheme of FIG. 3A, fed to the pipeline via the earthing plate 11 amperostatic currents oscillating between +0.75 and −0.75 mA, both of square wave (0.1 Hz) and of sinusoidal wave (0.1-0.3-1-3-5-10 Hz). The value of the excitation current was suitable for generating significant response signals without producing significant induced polarization.

Monitoring was conducted along a 106 meter length of pipeline at constant steps of 2 meters. Table 1 shows the relevant data. FIG. 7 shows the $R_p$ values measured along the length of pipeline; the deepest $R_p$ minima (indicated by the numbers 1 to 9) indicate the points most presumptive of corrosion underway. A check was made on the points of greatest depth by digging out the ground around the pipeline and examining the pipeline after removing the raised covering.

Points 1 and 2: a corrosion zone was identified of up to 4 mm deep, intermediate between the two points and with two swellings in the covering; at point 2 (98 m) a flaw was found in the raised covering extending towards point 1 (104 m), at which the ground had however not been removed.

Point 3: this was not considered because of the small peak depth.

Point 4: a number of flaws in various wrinkles in the covering were identified around point 4 (78 m), converging into a zone of incipient corrosion.

Point 5: a gathering of wrinkle flaws was found at point 5 (70 m), converging into a zone of incipient corrosion with $H_2S$-containing liquid present. A corrosion crater 5–6 mm deep was identified along the path of one wrinkle.

Point 6: a large zone of attack was identified, with a series of wrinkles with various flaws at point 6 (50 m). The zone concerned measures about 100 $cm^2$.

Point 7: corrosion was identified with craters of modest depth. From point 7 (46 m) wrinkle flaws originate, of maximum length 2.5–3 m, terminating in a corrosion zone.

Point 8: corrosion craters distributed over an area of 2000 $cm^2$ are present at point 8 (38 m), with a maximum depth of 3 mm.

Point 9: the ground was not removed here (6 m). The series of measurements identified points of detachment of the covering with corrosion underway on the basis of measured values of capacitive loss, and in addition, on the basis of ohmic loss values, gave useful information on the state of the covering where no detachment had taken place.

TABLE 1

Responses obtained by the measurement system, with a stainless steel/tantalum stake, on a pipeline portion by feeding sinusoidal waves and square waves of constant current (± 0.75 mA)

| Peak position (points) (meters) | Voltage wave at 5 Hz (mV) | Voltage wave at 0.1 Hz (mV) | Ohmic loss R.I. (mV)* | Capac. loss Rp.I. (mV)* | Polariz resistance (Ohm)* |
|---|---|---|---|---|---|
| 0 | 38.5 | 40.8 | 38.5 | 2.4 | 1.6 |
| 2 | 45.2 | 46.7 | 45.0 | 1.8 | 1.2 |
| 4 | 42.8 | 43.8 | 42.6 | 1.4 | 1.0 |
| 6(9) | 58.8 | 59.4 | 58.8 | 0.6 | 0.4 |
| 8 | 43.5 | 45.6 | 43.2 | 2.4 | 1.6 |
| 10 | 33.8 | 36.6 | 33.4 | 3.3 | 2.2 |
| 12 | 18.7 | 22.8 | 18.7 | 4.2 | 2.8 |
| 14 | 22.4 | 25.8 | 22.2 | 3.6 | 2.4 |
| 16 | 17.0 | 21.6 | 16.8 | 4.8 | 3.2 |
| 18 | 16.8 | 19.8 | 16.8 | 3.0 | 2.0 |
| 20 | 21.1 | 24.6 | 21.0 | 3.6 | 2.4 |
| 22 | 20.4 | 24.0 | 20.4 | 3.6 | 2.4 |
| 24 | 19.8 | 22.8 | 19.2 | 3.6 | 2.4 |
| 26 | 16.8 | 20.4 | 16.8 | 3.6 | 2.4 |
| 28 | 19.5 | 21.8 | 19.2 | 3.0 | 2.0 |
| 30 | 21.8 | 24.0 | 21.6 | 2.4 | 1.6 |
| 32 | 21.0 | 23.4 | 20.9 | 2.4 | 1.6 |
| 34 | 22.4 | 24.6 | 22.2 | 2.4 | 1.6 |
| 36 | 34.8 | 36.3 | 34.8 | 2.0 | 1.4 |
| 38(8) | 47.4 | 49.2 | 47.4 | 0.6 | 0.4 |
| 40 | 34.2 | 36.0 | 34.2 | 1.8 | 1.2 |
| 42 | 40.8 | 43.4 | 41.0 | 2.4 | 1.6 |
| 44 | 36.2 | 38.4 | 36.0 | 2.6 | 1.7 |
| 46(7) | 59.3 | 59.4 | 59.3 | 0.1 | 0.07 |
| 48 | 38.6 | 40.2 | 38.6 | 1.8 | 1.2 |
| 50(6) | 49.6 | 49.8 | 49.6 | 0.2 | 0.14 |
| 52 | 52.8 | 54.0 | 53.0 | 1.2 | 0.8 |
| 54 | 49.0 | 51.6 | 49.5 | 2.4 | 1.6 |
| 56 | 58.4 | 60.6 | 58.0 | 2.4 | 1.6 |
| 58 | 75.0 | 77.4 | 75.0 | 2.4 | 1.6 |
| 60 | 100.0 | 102.6 | 100.2 | 2.4 | 1.6 |

TABLE 1-continued

Responses obtained by the measurement system, with a stainless steel/tantalum stake, on a pipeline portion by feeding sinusoidal waves and square waves of constant current (± 0.75 mA)

| Peak position (points) (meters) | Voltage wave at 5 Hz (mV) | Voltage wave at 0.1 Hz (mV) | Ohmic loss R.I. (mV)* | Capac. loss Rp.I. (mV)* | Polariz resistance (Ohm)* |
|---|---|---|---|---|---|
| 62 | 70.7 | 73.8 | 70.5 | 3.0 | 2.0 |
| 64 | 59.4 | 61.8 | 59.4 | 2.4 | 1.6 |
| 66 | 57.6 | 60.0 | 58.0 | 2.4 | 1.6 |
| 68 | 46.4 | 48.0 | 46.8 | 1.5 | 1.0 |
| 70(5) | 45.8 | 46.8 | 45.6 | 1.2 | 0.8 |
| 72 | 30.9 | 33.0 | 30.7 | 2.4 | 1.6 |
| 74 | 58.2 | 60.6 | 58.2 | 2.4 | 1.6 |
| 76 | 37.8 | 41.4 | 37.8 | 3.4 | 2.4 |
| 78(4) | 54.4 | 56.0 | 54.2 | 0.6 | 0.4 |
| 80 | 63.0 | 63.8 | 63.4 | 1.0 | 0.7 |
| 82 | 49.8 | 52.2 | 49.8 | 2.4 | 1.6 |
| 84 | 71.6 | 74.4 | 72.0 | 3.0 | 2.0 |
| 86 | 70.2 | 72.0 | 70.2 | 1.8 | 1.2 |
| 88 | 63.2 | 64.8 | 63.0 | 1.8 | 1.2 |
| 90 | 39.6 | 45.0 | 39.8 | 5.4 | 3.6 |
| 92 | 58.3 | 60.6 | 58.6 | 2.4 | 1.6 |
| 94 | 36.0 | 39.6 | 36.0 | 3.6 | 2.4 |
| 96 | 67.2 | 69.6 | 67.2 | 2.4 | 1.6 |
| 98(2) | 52.8 | 54.0 | 52.8 | 1.2 | 0.8 |
| 100 | 31.8 | 34.8 | 32.0 | 3.0 | 2.0 |
| 102 | 35.2 | 37.2 | 35.6 | 1.8 | 1.2 |
| 104(1) | 44.0 | 45.0 | 44.2 | 1.2 | 0.8 |
| 106 | 128.2 | 130.2 | 128.4 | 1.8 | 1.2 |

*Data also verified by the square wave at 0.1 Hz.

We claim:

1. A method for monitoring the state of, and for locating detachment of, a protective covering of an immersed or buried structure subjected to cathodic protection with constant current, comprising the steps of:
applying local sinusoidal wave excitation currents of different frequencies to the structure;
measuring a plurality of voltage responses corresponding to the different frequencies applied to the structure;
comparing the measured voltage responses to each other; and
determining, on the basis of voltage response differences or coincidences at the various frequencies, whether there is detachment of the protective covering or whether there is only decay in the protective covering.

2. The method for monitoring the state of, and for locating detachment of, the protective covering of an immersed or buried structure according to claim 1, wherein the step of applying local sinusoidal wave excitation currents of different frequencies to the structure comprises the step of applying at least two trains of sinusoidal current waves between 0.1 and 10.0 mA in amplitude, at frequencies of between $10^{-3}$ and 30 Hz, the ratio of their frequencies being between 10 and 1000.

3. The method for monitoring the state of, and for locating detachment of, the protective covering of an immersed or buried structure according to claim 2, wherein the step of applying the excitation currents to the structure comprises the step of applying at least two trains of sinusoidal current waves between 0.1 and 10.0 mA in magnitude, at frequencies of between $10^{-3}$ and 30 Hz, the ratio of their frequencies being between 40 and 100.

4. The method for monitoring the state of, and for locating detachment of, the protective covering of an immersed or buried structure according to claim 2, wherein the step of applying the excitation currents to the structure comprises the step of applying each wave train at a duration of 3 to 10 cycles.

5. The method for monitoring the state of, and for locating detachment of, the protective covering of an immersed or buried structure according to any one of claims 2-4, wherein said step of applying the excitation currents to the structure comprises the step of applying square wave excitation current trains at a plurality of points along the structure wherein said square wave excitation current trains have equal intensity in order to verify that the R.I. signal responses to the square wave coincide substantially with the amplitude of the signal obtained with the highest frequency sinusoidal current, and that the total response amplitudes to the square wave coincide substantially with the amplitude of the signal obtained with the lowest frequency sinusoidal current.

6. The method for monitoring the state of, and for locating detachment of, the protective covering of an immersed or buried structure according to claim 5, wherein said step of applying square wave excitation current trains comprises the step of applying said square wave excitation current trains irregularly at said plurality of points along the structure.

7. The method for monitoring the state of, and for locating detachment of, the protective covering of an immersed or buried structure according to claim 5, wherein the step of applying the excitation current to the structure comprises the step of selecting the frequency of the square wave excitation current signal trains to be in the range of 0.1–0.01 Hz.

8. The method for monitoring the state of, and for locating detachment of, the protective covering of an immersed or buried structure according to claim 5, wherein the measuring step comprises the steps of:
taking measurements by positioning a stake along the structure at discrete intervals; and
emitting an excitation current signal at said discrete intervals and measuring the corresponding voltage responses.

9. The method for monitoring the state of, and for locating detachment of, the protective covering of an immersed or buried structure according to claim 8, wherein the step of taking measurements by positioning said stake along the structure at discrete intervals comprises the step of taking measurements by positioning said stake along the structure at intervals of 2 to 10 meters.

10. The method for monitoring the state of, and for locating detachment of, the protective covering of an immersed or buried structure according to claim 1, further comprising the step of dividing the peak-to-peak voltage differences between the signals measured at low frequencies and those measured at high frequencies by the intensity of the sinusoidal wave excitation currents, the measured values indicating a polarization resistance $R_p$ within a portion of the structure corresponding to the position of the peak, the minimum values corresponding to points at which corrosion has occurred and the depth of the minimum values corresponding to the intensity of the corrosion.

* * * * *